US011432728B2

(12) United States Patent
Mori et al.

(10) Patent No.: US 11,432,728 B2
(45) Date of Patent: Sep. 6, 2022

(54) BLOOD PRESSURE/PULSE WAVE MEASUREMENT DEVICE AND PROGRAM

(71) Applicant: Fukuda Denshi Co., Ltd., Tokyo (JP)

(72) Inventors: Naoki Mori, Kyoto (JP); Mayuko Kaneda, Kyoto (JP); Masahiko Yumoto, Kyoto (JP); Kazuhiro Matsui, Kyoto (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 32 days.

(21) Appl. No.: 16/084,589

(22) PCT Filed: Oct. 31, 2016

(86) PCT No.: PCT/JP2016/082320

§ 371 (c)(1),
(2) Date: Sep. 13, 2018

(87) PCT Pub. No.: WO2017/158908

PCT Pub. Date: Sep. 21, 2017

(65) Prior Publication Data

US 2019/0076034 A1 Mar. 14, 2019

(30) Foreign Application Priority Data

Mar. 16, 2016 (JP) ............................ JP2016-052597

(51) Int. Cl.
*A61B 5/022* (2006.01)
*A61B 5/00* (2006.01)
(Continued)

(52) U.S. Cl.
CPC .......... *A61B 5/02225* (2013.01); *A61B 5/022* (2013.01); *A61B 5/02007* (2013.01);
(Continued)

(58) Field of Classification Search
CPC ............ A61B 5/02225; A61B 5/02007; A61B 5/02108; A61B 5/02125; A61B 5/022;
(Continued)

(56) References Cited

U.S. PATENT DOCUMENTS 6,355,000 B1 3/2002 Ogura
2004/0171940 A1 9/2004 Narimatsu
(Continued)

FOREIGN PATENT DOCUMENTS

JP 2000-316821 A 11/2000
KR 1020110102304 A 9/2011
WO 2010/035629 A1 4/2010

OTHER PUBLICATIONS

International Search Report from International Application No. PCT/JP2016/082320 dated Jan. 10, 2017.
(Continued)

*Primary Examiner* — Daniel L Cerioni
*Assistant Examiner* — Deirdre M Willgohs
(74) *Attorney, Agent, or Firm* — Brundidge & Stanger, P.C.

(57) ABSTRACT

This blood pressure/pulse wave measurement device obtains a pulse wave velocity (baPWV) that is an index representing the arterial stiffness of a subject. A lower limb/upper limb blood pressure ratio (ABI) that is an index representing the clogging of the blood vessels of a subject is obtained. When the lower limb/upper limb blood pressure ratio (ABI) of the subject surpasses a preset first threshold value, a point (Px) representing the pulse wave velocity (baPWV) is displayed on a one-dimensional graph (46). When the lower limb/upper limb blood pressure ratio (ABI) of the subject is equal to or less than the preset first threshold value, a point representing the lower limb/upper limb blood pressure ratio (ABI) is displayed on the one-dimensional graph (46)
(Continued)

instead of the point representing the pulse wave velocity (baPWV).

6 Claims, 12 Drawing Sheets

(51) Int. Cl.
*A61B 5/02* (2006.01)
*A61B 5/021* (2006.01)
*A61B 5/0285* (2006.01)
*A61B 5/0235* (2006.01)

(52) U.S. Cl.
CPC ...... *A61B 5/02108* (2013.01); *A61B 5/02125* (2013.01); *A61B 5/742* (2013.01); *A61B 5/0235* (2013.01); *A61B 5/0285* (2013.01); *A61B 5/02141* (2013.01)

(58) Field of Classification Search
CPC ... A61B 5/742; A61B 5/02141; A61B 5/0235; A61B 5/0285
USPC .......................................................... 600/500
See application file for complete search history.

(56) References Cited

U.S. PATENT DOCUMENTS

2011/0224558 A1 9/2011 Kobayashi
2011/0230774 A1 9/2011 Kobayashi et al.
2012/0095353 A1 4/2012 Mori et al.
2015/0317810 A1* 11/2015 Grunwald ............... G06F 3/011 345/440.1

OTHER PUBLICATIONS

Extended European Search Report for 16894525.1 dated Sep. 18, 2019, 8 pages.
Hirofumi Tomiyama, et al.: Brachial-Ankle PWV: Current Status and Future Directions as a Useful Marker in the Management of Cardiovascular Disease and/or Cardiovascular Risk Factors, Journal of Atherosclerosis and Thrombosis, vol. 23, No. 2, Feb. 1, 2016, pp. 128-146.
Office Action dated Dec. 20, 2018 for the corresponding Australian Patent Application No. 2016398145.

* cited by examiner

BLOOD PRESSURE/PULSE WAVE MEASUREMENT DEVICE AND PROGRAM

TECHNICAL FIELD

The present invention relates to a blood pressure pulse wave measurement apparatus, and more particularly to a blood pressure pulse wave measurement apparatus for obtaining and displaying a pulse wave velocity that is an index representing stiffness of blood vessels, and a lower/upper limb blood pressure ratio that is an index representing clogging of blood vessels to represent a progress stage of arteriosclerosis of a subject.

The present invention also relates to a program for causing a computer to perform a method of displaying a pulse wave velocity and a lower/upper limb blood pressure ratio to represent a progress stage of arteriosclerosis of a subject.

BACKGROUND ART

Conventionally, as this type of blood pressure pulse wave measurement apparatus, for example, as disclosed in PTL 1 (Japanese Patent Application Laid-Open No. 2000-316821), an apparatus is known for obtaining a brachial-ankle pulse wave velocity (baPWV) that is an index representing stiffness of blood vessels, and an ankle brachial index (ABI) that is an index representing clogging of blood vessels, which are plotted on the ordinate and the abscissa, respectively, and displaying the two indexes as one point on a two-dimensional graph to represent a progress stage of arteriosclerosis of a subject.

CITATION LIST

Patent Literature

PTL 1

Japanese Patent Application Laid-Open No. 2000-316821

SUMMARY OF INVENTION

Technical Problem

Observing the two-dimensional graph described above, a cardiologist can accurately understand a progress stage of arteriosclerosis of a patient. However, it is difficult for, for example, an ordinary patient or medical personnel not specializing in that field (hereinafter referred to as "ordinary patient etc.") to intuitively understand a progress stage of arteriosclerosis.

Thus, an object of the present invention is to provide a blood pressure pulse wave measurement apparatus capable of displaying a progress stage of arteriosclerosis to be intuitively understandable by an ordinary patient etc.

Another object of the present invention is to provide a program for causing a computer to perform a method of displaying a progress stage of arteriosclerosis to be intuitively understandable by an ordinary patient etc.

Solution to Problem

In order to solve the above problem, a blood pressure pulse wave measurement apparatus of the present invention for displaying a progress stage of arteriosclerosis of a subject includes:

a pulse wave velocity obtaining section that obtains a pulse wave velocity that is an index representing stiffness of blood vessels of the subject;

a lower/upper limb blood pressure ratio obtaining section that obtains a lower/upper limb blood pressure ratio that is an index representing clogging of blood vessels of the subject; and a display processing section that performs processing to display a point representing the pulse wave velocity on a one-dimensional graph when the lower/upper limb blood pressure ratio of the subject exceeds a first threshold, the first threshold being predefined, and to display a point representing the lower/upper limb blood pressure ratio instead of the point representing the pulse wave velocity on the one-dimensional graph when the lower/upper limb blood pressure ratio of the subject is the first threshold or less.

The pulse wave velocity herein typically refers to brachial-ankle pulse wave velocity baPWV, but may refer to heart-ankle pulse wave velocity (haPWV) or cardio-ankle vascular index (CAVI) based thereon. The lower/upper limb blood pressure ratio typically refers to ankle brachial index ABI.

The pulse wave velocity obtaining section may measure and obtain a pulse wave velocity or may obtain a measured pulse wave velocity input thereto. Similarly, the lower/upper limb blood pressure ratio obtaining section may measure and obtain a lower/upper limb blood pressure ratio or obtain a measured lower/upper limb blood pressure ratio input thereto.

The first threshold being "predefined" refers to the first threshold being defined by a determination rule for determining a progress stage of arteriosclerosis, typically, by the Steno-Stiffness chart disclosed such as in "Akira Yamashina et al., Symposium Report of 14th Clinical Blood Pressure Pulse Wave Society, "Arterial Stiffness 2014"; 20:36-9".

A display medium on which the display processing section "displays" may be, for example, a display screen of a liquid crystal display (LCD) or the like, or paper output by a printer.

The "point" representing the pulse wave velocity and the "point" representing the lower/upper limb blood pressure ratio may substantially represent only points on the one-dimensional graph, that is, coordinate positions. For example, to represent the "points", symbols such as a circle or a triangle, marks, or the like may be used.

In the blood pressure pulse wave measurement apparatus of the present invention, the pulse wave velocity obtaining section obtains the pulse wave velocity that is the index representing stiffness of blood vessels of the subject. Also, the lower/upper limb blood pressure ratio obtaining section obtains the lower/upper limb blood pressure ratio that is the index representing clogging of blood vessels of the subject. The display processing section performs processing to display the point representing the pulse wave velocity on the one-dimensional graph when the lower/upper limb blood pressure ratio of the subject exceeds the first threshold, while displays the point representing the lower/upper limb blood pressure ratio instead of the point representing the pulse wave velocity on the one-dimensional graph when the lower/upper limb blood pressure ratio of the subject is the first threshold or less.

Generally, in medical terms, at a relatively early stage of progress of arteriosclerosis, the pulse wave velocity is more noted than the lower/upper limb blood pressure ratio, and at a later stage of the progress of arteriosclerosis, the lower/upper limb blood pressure ratio is more noted than the pulse wave velocity. In the blood pressure pulse wave measurement apparatus of the present invention, when the lower/upper limb blood pressure ratio of the subject exceeds the first threshold, that is, at the relatively early stage of the progress of arteriosclerosis, the point representing the pulse wave velocity is displayed on the one-dimensional graph. On the other hand, when the lower/upper limb blood pressure ratio of the subject is the first threshold or less, that is, at the later stage of the progress of arteriosclerosis, the point representing the lower/upper limb blood pressure ratio instead of the point representing the pulse wave velocity is displayed on the one-dimensional graph. Specifically, in accordance with the progress stage of arteriosclerosis, the point representing the pulse wave velocity to be noted and the point representing the lower/upper limb blood pressure ratio to be noted are switched and displayed on the one-dimensional graph. As a result, an ordinary patient etc. can easily understand the progress stage of arteriosclerosis according to a coordinate position of the point displayed on the one-dimensional graph. As such, with the blood pressure pulse wave measurement apparatus, the progress stage of arteriosclerosis can be displayed to be intuitively understandable by the ordinary patient etc.

In the blood pressure pulse wave measurement apparatus of an embodiment, the first threshold of an ankle brachial index (ABI) as the lower/upper limb blood pressure ratio is set to 0.90 based on the Steno-Stiffness chart.

The Steno-Stiffness chart defines that a normal range of the ankle brachial index (ABI) is $1.00 \leq ABI \leq 1.40$ with two decimal places as significant digits. Also, ABI=0.90 is defined to be a lower limit of a boundary zone.

In this blood pressure pulse wave measurement apparatus of an embodiment, the first threshold of an ankle brachial index (ABI) as the lower/upper limb blood pressure ratio is set to 0.90 based on the Steno-Stiffness chart. Thus, the pulse wave velocity and the lower/upper limb blood pressure ratio can be properly switched on the one-dimensional graph according to the Steno-Stiffness chart.

The blood pressure pulse wave measurement apparatus of an embodiment further includes:

an upstroke time obtaining section that obtains an upstroke time (UT) of a pulse wave in the ankle of the subject; and a normalized pulse wave area obtaining section that obtains a normalized pulse wave area (% MAP) of a waveform of the pulse wave in the ankle of the subject, in which the display processing section performs processing to display a point representing the ankle brachial index (ABI) as the lower/upper limb blood pressure ratio instead of the point representing the pulse wave velocity on the one-dimensional graph when the upstroke time (UT) is 180 milliseconds or more or when the normalized pulse wave area (% MAP) is 45% or more in the case where the ankle brachial index (ABI) is more than the first threshold of 0.90 and less than a second threshold of 1.00.

The upstroke time (UT) herein refers to, as illustrated in FIG. 5A, a time from a rise to a peak of pulse waveform PW (in milliseconds). The upstroke time (UT) is short for a normal sharp waveform, while is long with stenosis or occlusion of blood vessels. The normalized pulse wave area (% MAP) refers to, as illustrated in FIG. 5B, a percentage of area average value S of pulse waveform PW of the ankle divided by amplitude A (in %). The normalized pulse wave area (% MAP) is low for a normal sharp waveform, while is high with stenosis or occlusion of blood vessels which causes the waveform to lose sharpness.

In this blood pressure pulse wave measurement apparatus of an embodiment, the display processing section performs processing to display a point representing the ankle brachial index (ABI) as the lower/upper limb blood pressure ratio instead of the point representing the pulse wave velocity on the one-dimensional graph when the upstroke time (UT) is 180 milliseconds or more or when the normalized pulse wave area (% MAP) is 45% or more in the case where the ankle brachial index (ABI) is more than the first threshold of 0.90 and less than a second threshold of 1.00. Thus, the pulse wave velocity and the lower/upper limb blood pressure ratio can be more properly switched on the one-dimensional graph according to the Steno-Stiffness chart.

In the blood pressure pulse wave measurement apparatus of an embodiment, the display processing section provides a display to represent blood vessels being calcified if the ankle brachial index (ABI) exceeds a third threshold of 1.40.

In this blood pressure pulse wave measurement apparatus of an embodiment, the display processing section provides a display to represent blood vessels being calcified if the ankle brachial index (ABI) exceeds a third threshold of 1.40. Thus, it can be notified that the subject is in a particularly severe condition with calcified blood vessels.

In the blood pressure pulse wave measurement apparatus of an embodiment, when a plurality of measurements of the pulse wave velocity and the lower/upper limb blood pressure ratio cause the lower/upper limb blood pressure ratio to transit across the first threshold, the display processing section sets a scale of the one-dimensional graph so that the point representing the pulse wave velocity and the point representing the lower/upper limb blood pressure ratio gradually move in the same direction on the one-dimensional graph.

In this blood pressure pulse wave measurement apparatus of an embodiment, when a plurality of measurements of the pulse wave velocity and the lower/upper limb blood pressure ratio cause the lower/upper limb blood pressure ratio to transit across the first threshold, the display processing section sets a scale of the one-dimensional graph so that the point representing the pulse wave velocity and the point representing the lower/upper limb blood pressure ratio gradually move in the same direction on the one-dimensional graph. Thus, the progress stage of arteriosclerosis can be displayed to be more intuitively understandable by the ordinary patient etc.

In the blood pressure pulse wave measurement apparatus of an embodiment, the display processing section performs processing to display illustration representing a state of blood vessels according to the progress stage of arteriosclerosis in addition to the one-dimensional graph.

In the blood pressure pulse wave measurement apparatus of an embodiment, the display processing section performs processing to display illustration representing a state of blood vessels according to the progress stage of arteriosclerosis in addition to the one-dimensional graph. Thus, the progress stage of arteriosclerosis can be displayed to be further intuitively understandable by the ordinary patient etc.

In another aspect, a program of the present invention causes a computer to perform a method of displaying a progress stage of arteriosclerosis of a subject, in which the method includes:

obtaining a pulse wave velocity that is an index representing stiffness of blood vessels of the subject, and obtaining a lower/upper limb blood pressure ratio that is an index representing clogging of blood vessels of the subject; and performing processing to display a point representing the pulse wave velocity on a one-dimensional graph when the lower/upper limb blood pressure ratio of the subject exceeds a first threshold, the first threshold being predefined, and to display a point representing the lower/upper limb blood pressure ratio instead of the point representing the pulse wave velocity on the one-dimensional graph when the lower/upper limb blood pressure ratio of the subject is the first threshold or less.

If the program of the present invention causes the computer to perform the method, when the lower/upper limb blood pressure ratio of the subject exceeds the first threshold, that is, at a relatively early stage of the progress of arteriosclerosis, the point representing the pulse wave velocity is displayed on the one-dimensional graph. On the other hand, when the lower/upper limb blood pressure ratio of the subject is the first threshold or less, that is, at a later stage of the progress of arteriosclerosis, the point representing the lower/upper limb blood pressure ratio instead of the point representing the pulse wave velocity is displayed on the one-dimensional graph. Specifically, in accordance with the progress stage of arteriosclerosis, the point representing the pulse wave velocity to be noted and the point representing the lower/upper limb blood pressure ratio to be noted are switched and displayed on the one-dimensional graph. As a result, an ordinary patient etc. can easily understand the progress stage of arteriosclerosis according to a coordinate position of the point displayed on the one-dimensional graph. As such, by the computer performing the method according to the program of the present invention, the progress stage of arteriosclerosis can be displayed to be intuitively understandable by the ordinary patient etc.

Advantageous Effects of Invention

As is apparent from the above, with the blood pressure pulse wave measurement apparatus of the present invention, the progress stage of arteriosclerosis can be displayed to be intuitively understandable by the ordinary patient etc.

Also, by the computer performing the method according to the program of the present invention, the progress stage of arteriosclerosis can be displayed to be intuitively understandable by the ordinary patient etc.

DESCRIPTION OF EMBODIMENTS

Embodiments of the present invention will be described in detail with reference to the accompanying drawings.

Figure 1:
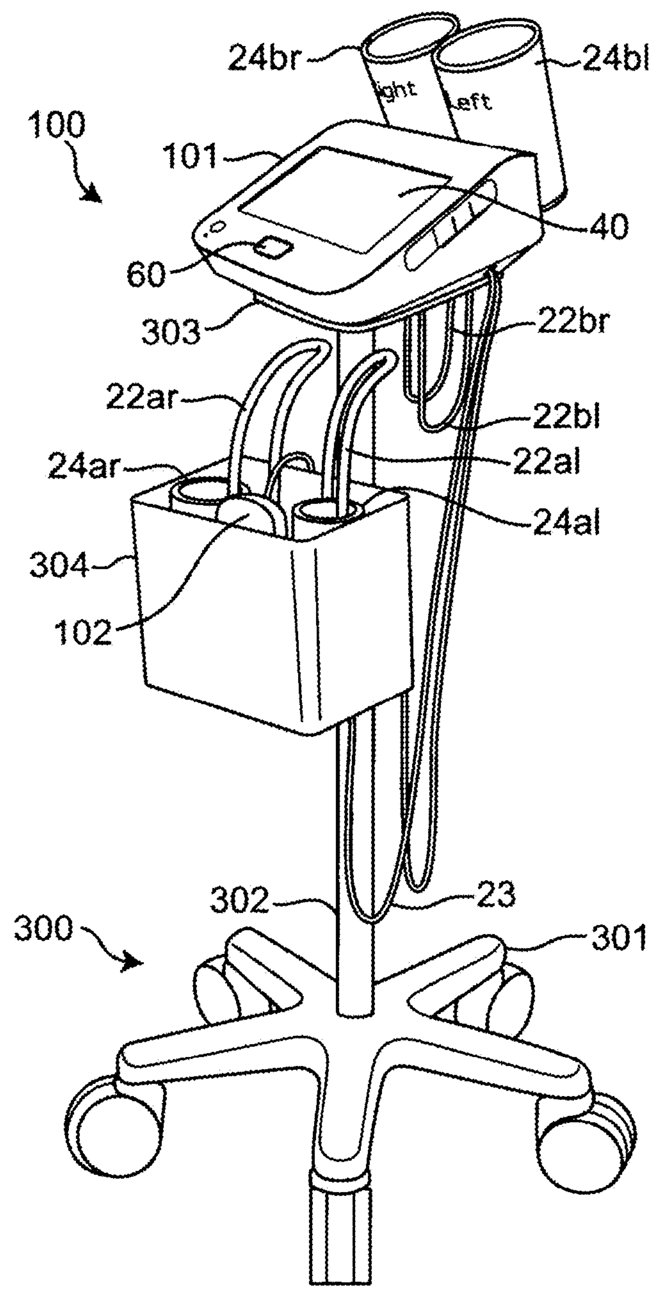
FIG. 1 is a perspective view of a blood pressure pulse wave measurement apparatus according to an embodiment of the present invention being housed in a housing wagon.

FIG. 1 shows blood pressure pulse wave measurement apparatus 100 according to an embodiment of the present invention being housed in housing wagon 300. Blood pressure pulse wave measurement apparatus 100 includes main unit 101, ankle unit 102, and four cuffs 24*ar*, 24*al*, 24*br*, 24*bl*. Housing wagon 300 includes leg 301 with casters, post 302 standing on leg 301, placing table 303 mounted to an end of post 302, and housing box 304 mounted in the middle of post 302 and opening upward. On placing table 303, main unit 101 is placed. In housing box 304, ankle unit 102 and cuffs 24*ar*, 24*al* for the right ankle (right lower limb) and left ankle (left upper limb) are housed. Cuffs 24*br*, 24*bl* for the right upper arm (right upper limb) and left upper arm (left upper limb) are hung and held on hooks 101*e*, 101*f* (shown in FIG. 2) provided in the rear of main unit 101.

Ankle unit 102 and cuffs 24*ar*, 24*al* for the right ankle (right lower limb) and left ankle (left upper limb) are connected by tubes 22*ar*, 22*al* through which air for pressurizing the cuffs is passed. Similarly, main unit 101 and cuffs 24*br*, 24*bl* for the right upper arm (right upper limb) and left upper arm (left upper limb) are connected by tubes 22*br*, 22*bl* through which air for pressurizing the cuffs is passed. Main unit 101 is connected to ankle unit 102 by connection cable 23 so as to be able to supply power and communicate.

Figure 2:
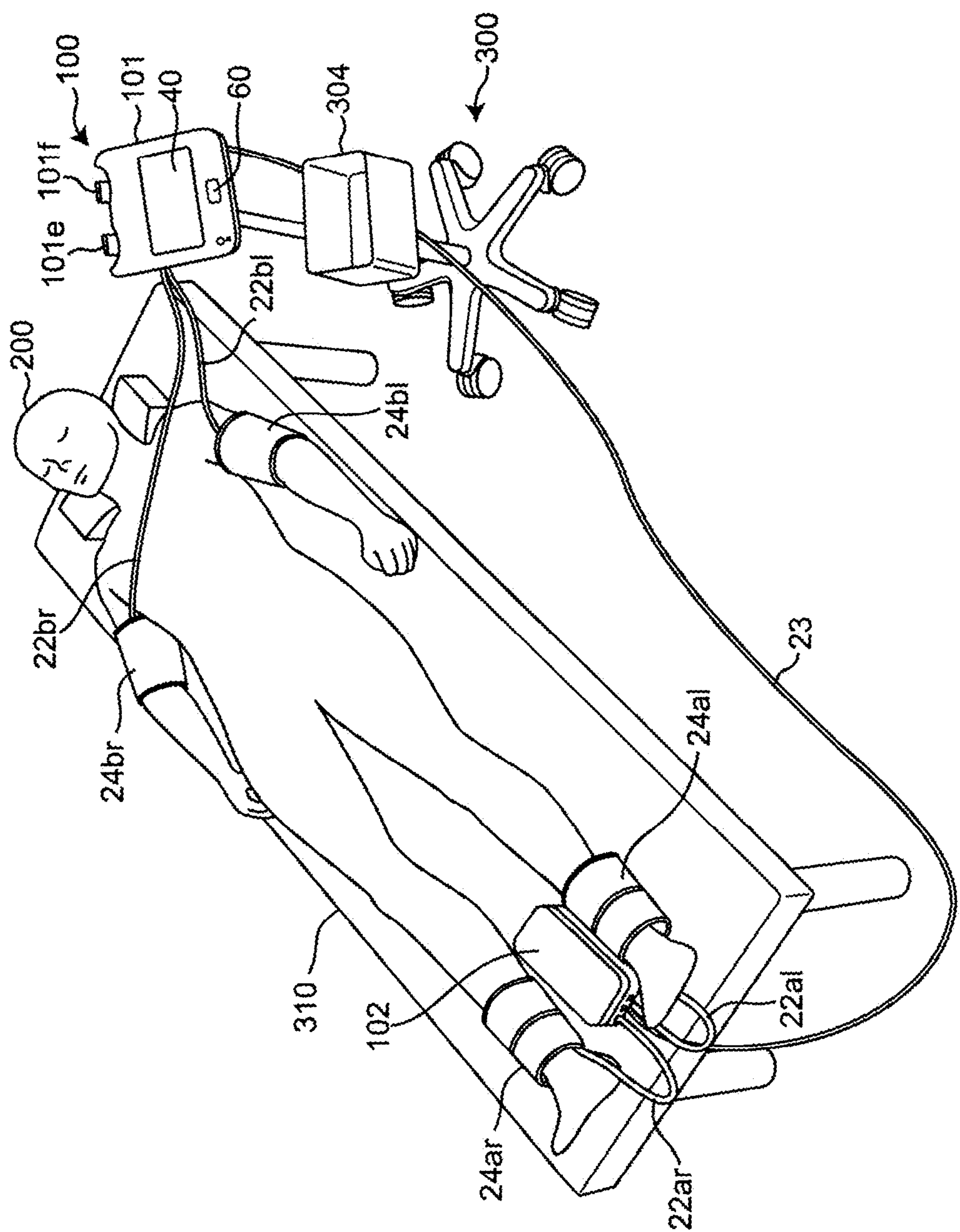
FIG. 2 is a perspective view of the blood pressure pulse wave measurement apparatus being used.

FIG. 2 shows blood pressure pulse wave measurement apparatus 100 being used. Subject 200 is lying on his/her back on bed 310. Ankle unit 102 is taken out of housing box 304, and placed between the right ankle and left ankle of subject 200 on bed 310.

Cuffs 24*ar*, 24*al*, 24*br*, 24*bl* are fitted around the limbs of subject 200. Specifically, cuffs 24*ar*, 24*al*, 24*br*, 24*bl* are fitted around the right ankle (right lower limb), left ankle (left upper limb), right upper arm (right upper limb), and left upper arm (left upper limb), respectively. An example of the cuffs being fitted only around the right ankle, left ankle, right upper arm, left upper arm are described below. However, the "limbs" refer to sites included in four limbs, and may include the wrist, fingertip, or the like. Cuffs 24*ar*, 24*al*, 24*br*, 24*bl* are collectively called "cuff 24" unless there is a need to make a distinction.

Figure 3:
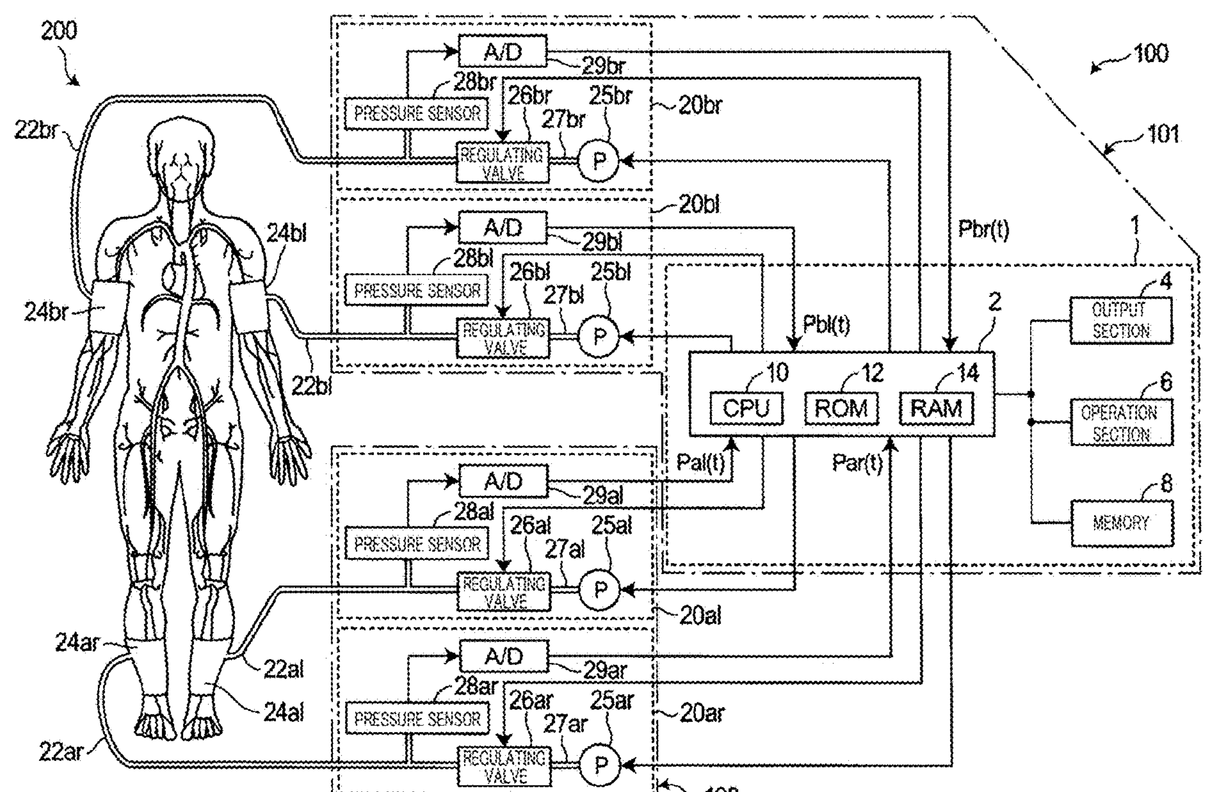
FIG. 3 shows a block configuration of a control system of the blood pressure pulse wave measurement apparatus.

FIG. 3 shows a block configuration of a control system of blood pressure pulse wave measurement apparatus 100. Ankle unit 102 includes two detection units 20*ar*, 20*al*. Main unit 101 includes information processing unit 1 and two detection units 20*br*, 20*bl*.

Detection units 20*ar*, 20*al*, 20*br*, 20*bl* each include hardware required for detecting a pulse wave in the limbs of subject 200. Detection units 20*ar*, 20*al*, 20*br*, 20*bl* may all have the same configuration, and thus are collectively called "detection unit 20" unless there is a need to make a distinction.

Information processing unit 1 includes control section 2, output section 4, operation section 6, and memory 8.

Control section 2 controls entire blood pressure pulse wave measurement apparatus 100, and is constituted by a computer typically including central processing unit (CPU) 10, read only memory (ROM) 12, and random access memory (RAM) 14.

CPU 10 corresponds to an arithmetic processing section, reads a program previously stored in ROM 12, and executes the program using RAM 14 as a work memory.

Output section 4, operation section 6, and memory 8 are connected to control section 2. Output section 4 outputs a measured pulse wave, analysis results of the pulse wave, or the like. Output section 4 may be a display device constituted by a light emitting diode (LED), a liquid crystal display (LCD), or the like, or may be a printer (driver). In this example, as shown in FIGS. 1 and 2, display screen 40 of an LCD is provided as output section 4 on an upper surface of main unit 101.

Operation section 6 shown in FIG. 3 receives an instruction from a user. In this example, as shown in FIGS. 1 and 2, operation switch 60 is provided as operation section 6 on the upper surface of main unit 101. The user can use operation switch 60 to input instructions to power on/off, start blood pressure measurement, or the like.

Memory 8 shown in FIG. 3 holds various data or programs. CPU 10 of control section 2 reads or writes the data or programs recorded in memory 8. Memory 8 may be constituted by, for example, a hard disk, non-volatile memory (for example, flush memory), removable external recording medium, or the like.

Next, a configuration of each detection unit 20 will be described in detail.

Detection unit 20*br* adjusts and detects internal pressure of cuff 24*br* (hereinafter referred to as "cuff pressure") fitted around the right upper arm of subject 200 to detect a pulse wave in the right upper arm. Cuff 24*br* includes therein a fluid bag (an air bag in this example) (not shown).

Detection unit 20*br* includes pressure sensor 28*br*, regulating valve 26*br*, pressure pump 25*br*, analog to digital (A/D) converter 29*br*, and tube 27*br*. Cuff 24*br*, pressure sensor 28*br*, and regulating valve 26*br* are connected by tube 22*br*.

Pressure sensor 28*br* detects pressure fluctuations transmitted through tube 22*br*, and includes, as an example, a plurality of sensor elements arranged at regular intervals on a semiconductor chip of single crystal silicon or the like. A pressure fluctuation signal detected by pressure sensor 28*br* is converted into a digital signal by A/D converter 29*br* and input as pulse wave signal pbr(t) to control section 2.

Regulating valve 26*br* is interposed between pressure pump 25*br* and cuff 24*br*, and maintains pressure used for pressurizing cuff 24*br* within a predetermined range during measurement. Pressure pump 25*br* is actuated according to a detection instruction from control section 2, and supplies air to the fluid bag (not shown) in cuff 24*br* to pressurize cuff 24*br*.

The pressurization presses cuff 24*br* against a measurement site, and pressure changes according to the pulse wave in the right upper arm are transmitted through tube 22*br* to detection unit 20*br*. Detection unit 20*br* detects the transmitted pressure changes to detect the pulse wave in the right upper arm.

Detection unit 20*bl* similarly includes pressure sensor 28*bl*, regulating valve 26*bl*, pressure pump 25*bl*, A/D converter 29*bl*, and tube 27*bl*. Cuff 24*bl*, pressure sensor 28*bl*, and regulating valve 26*bl* are connected by tube 22*bl*.

Detection unit 20*ar* includes pressure sensor 28*ar*, regulating valve 26*ar*, pressure pump 25*ar*, A/D converter 29*ar*, and tube 27*ar*. Cuff 24*ar*, pressure sensor 28*ar*, and regulating valve 26*ar* are connected by tube 22*ar*.

Detection unit 20*al* similarly includes pressure sensor 28*al*, regulating valve 26*al*, pressure pump 25*al*, A/D converter 29*al*, and tube 27*al*. Cuff 24*al*, pressure sensor 28*al*, and regulating valve 26*al* are connected by tube 22*al*.

Functions of components in detection units 20*bl*, 20*ar*, 20*al* are the same as those in detection unit 20*br*, and thus detailed descriptions will not be repeated. Also, components in detection unit 20 will be described without symbols such as "ar" or "br" unless there is a need to make a distinction.

Figure 4:
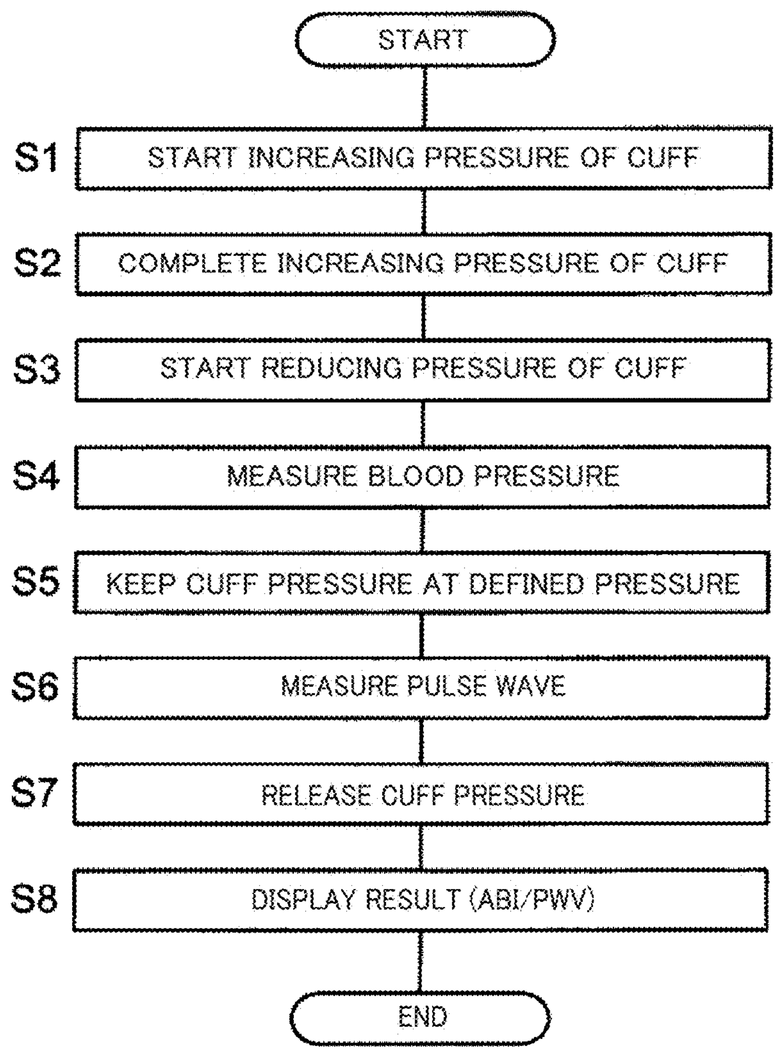
FIG. 4 shows a process flow of the blood pressure pulse wave measurement apparatus.

Blood pressure pulse wave measurement apparatus 100 measures a blood pressure value by a known oscillometric method using control with control section 2 (particularly CPU 10) as shown in a process flow in FIG. 4. Also, blood pressure pulse wave measurement apparatus 100 detects a pulse wave to obtain brachial-ankle pulse wave velocity baPWV as a pulse wave velocity, and obtain ankle brachial index ABI as a lower/upper limb blood pressure ratio. As known, brachial-ankle pulse wave velocity baPWV is an index representing stiffness of blood vessels, and ankle brachial index ABI is an index representing clogging of blood vessels.

Specifically, when the measurement is started, as shown in step S1 in FIG. 4, CPU 10 drives pump 25 in each detection unit 20 to start increasing pressure of each cuff 24. Then, as shown in step S2, with pressure sensor 28 monitoring cuff pressure, cuff pressure is increased to predetermined pressure (pressure higher than maximum blood pressure of subject 200) to stop pump 25 (COMPLETE INCREASING PRESSURE OF CUFF). Then, as shown in step S3, regulating valve 26 is controlled to start reducing pressure of each cuff 24 to gradually reduce the cuff pressure. In the pressure reducing process, fluctuations in arterial volume that occur in the artery of the measurement site are detected as a pulse wave signal by pressure sensor 28 via each cuff 24. As shown in step S4, based on an amplitude of the pulse wave signal, a predetermined algorithm by the known oscillometric method is used to calculate maximum blood pressure (systolic blood pressure) and minimum blood pressure (diastolic blood pressure) (MEASURE BLOOD PRESSURE). In addition, CPU 10 serves as a lower/upper limb blood pressure ratio obtaining section to calculate ankle brachial index ABI=(ankle systolic blood pressure)/(brachial systolic blood pressure) for each of the left and right sides of the body of subject 200. In this example, a pulse (in beats per minute) is also calculated. The blood pressure may be calculated in the pressure increasing process, not limited to the pressure reducing process.

Figure 6:
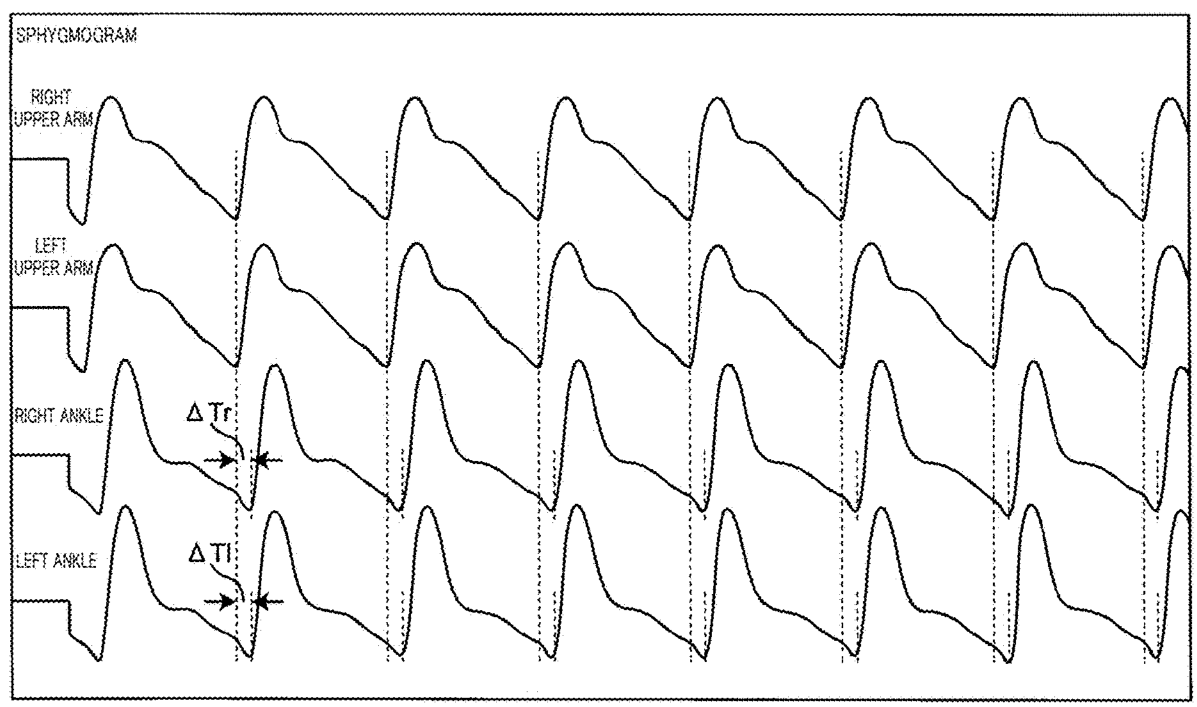
FIG. 6 shows pulse waveforms detected by a pressure sensor of the blood pressure pulse wave measurement apparatus.

Next, as shown in step S5, regulating valve 26 is closed to keep the cuff pressure at defined pressure (for example, about 50 mmHg). In this state, as shown in step S6, CPU 10 serves as a pulse wave velocity obtaining section to cause pressure sensor 28 to measure a pulse wave. At this time, pulse waveforms, for example, as shown in FIG. 6 are obtained. In this example, a delay of a rise of a waveform in the left ankle with respect to a rise of a waveform in the right upper arm of subject 200 is ΔT1. A delay of a rise of a waveform in the right ankle with respect to the rise of the waveform in the right upper arm of subject 200 is ΔTr. Based on delays ΔT1, ΔTr, brachial-ankle pulse wave velocity baPWV between the right upper arm and left ankle and brachial-ankle pulse wave velocity baPWV between the right upper arm and right ankle of subject 200 are calculated by the following equation:

$$baPWV=(La-Lb)/\Delta T,$$

where La denotes a distance from the aortic root to ankle, and Lb denotes a distance from the aortic root to upper arm.

ΔT represents ΔT1 or ΔTr (for simplicity, symbols "l" and "r" are omitted). Brachial-ankle pulse wave velocities baPWV calculated with ΔT1 and ΔTr are referred to as brachial-ankle pulse wave velocity baPWV for the left side of the body and brachial-ankle pulse wave velocity baPWV for the right side of the body, respectively.

Figure 5:
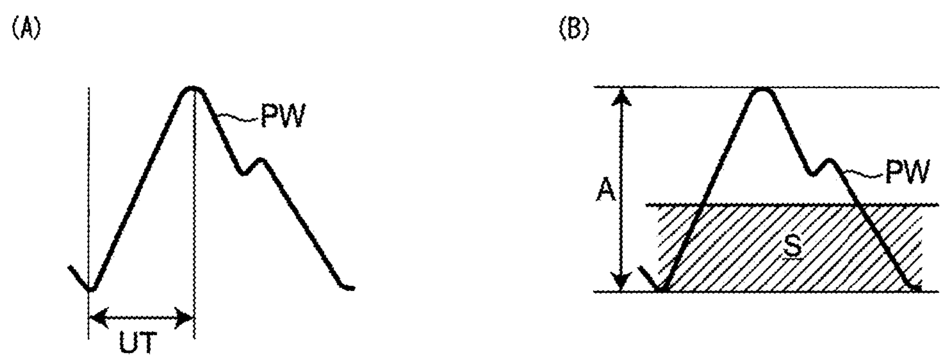
FIG. 5A illustrates upstroke time UT.
FIG. 5B illustrates normalized pulse wave area % MAP.

In this example, CPU 10 further serves as an upstroke time obtaining section to obtain upstroke time UT (in millisecond (ms)) from a rise to a peak of pulse waveform PW as shown in FIG. 5A. Further, CPU 10 serves as a normalized pulse wave area obtaining section to obtain normalized pulse wave area % MAP (in %) as shown in FIG. 5B.

Once the measurement is completed, as shown in step S7 in FIG. 4, regulating valve 26 is fully opened to release the cuff pressure. Then, as shown in step S8, CPU 10 serves as a display processing section to display a measurement result on display screen 40 (see FIG. 2) provided on the upper surface of main unit 101.

Figure 8:
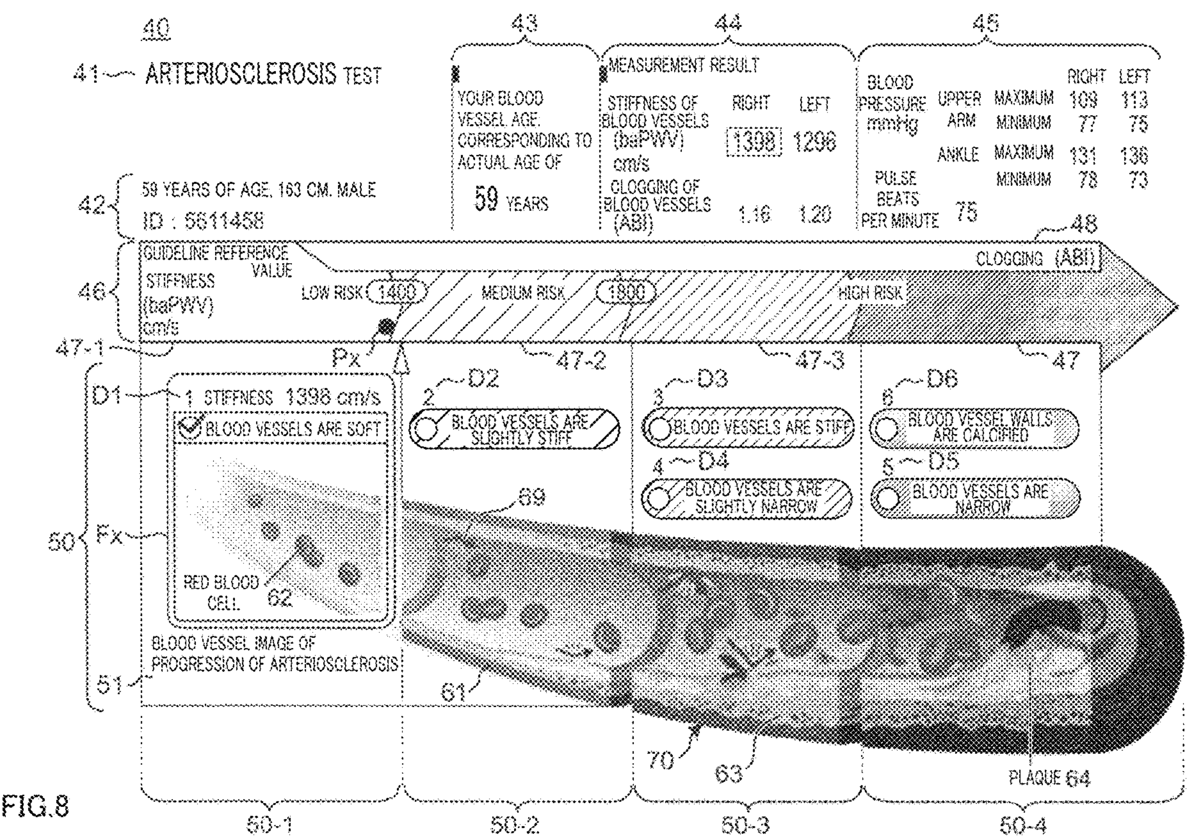
FIG. 8 shows Display Example 1 by the blood pressure pulse wave measurement apparatus.

FIGS. 8 to 13 show display examples displayed as measurement results on display screen 40. For example, as shown in FIG. 8, on display screen 40, title block 41 with a string of "ARTERIOSCLEROSIS TEST" located at an upper left corner, subject identification block 42 located below block 41, blood vessel age block 43 located on the right of blocks 41, 42 and indicating, by a numerical value, blood vessel age of subject 200, measurement result block 44 located on the right of block 43 and indicating, by numerical values, measurement results of brachial-ankle pulse wave velocity baPWV and ankle brachial index ABI, and blood pressure and pulse block 45 located on the right of block 44 and indicating, by numerical values, maximum blood pressure and minimum blood pressure in the upper arm and ankle and a pulse are provided. Further, one-dimensional graph 46 extending from the left to right of display screen 40 is provided along lower sides of blocks 41 to 45. Further, image block 50 displaying an image of blood vessels in which arteriosclerosis progresses by illustration is provided along a lower side of one-dimensional graph 46.

In subject identification block 42, age, height, and sex of subject 200 are displayed such as "59 YEARS OF AGE, 163 CM, MALE", and an identification number for identifying subject 200 is displayed such as "ID: 5611458".

In blood vessel age block 43, blood vessel age of subject 200 (a numerical value indicating a state of blood vessels of subject 200 by corresponding age of an average human) is displayed such as "YOUR BLOOD VESSEL AGE: CORRESPONDING TO ACTUAL AGE OF 59 YEARS".

In measurement result block 44, numerical values representing brachial-ankle pulse wave velocity baPWV and ankle brachial index ABI measured for the right and left sides of the body of subject 200 by the flow in FIG. 4 are displayed. In the example in FIG. 8, for brachial-ankle pulse wave velocity baPWV, "STIFFNESS OF BLOOD VESSELS (baPWV) CM/S: (RIGHT) 1398, (LEFT) 1296" is displayed for the right and left sides of the body. Also, for ankle brachial index ABI, "CLOGGING OF BLOOD VESSELS (ABI): (RIGHT) 1.16, (LEFT) 1.20" is displayed for the right and left sides of the body.

In blood pressure and pulse block 45, maximum blood pressure and minimum blood pressure in the upper arm, maximum blood pressure and minimum blood pressure in the ankle (in mmHg), and a pulse (in beats per minute) measured for the right and left sides of the body of subject 200 by the flow in FIG. 4 are displayed with numerical values. In the example in FIG. 8, for the upper arm, "MAXIMUM: (RIGHT) 109, (LEFT) 113", "MINIMUM: (RIGHT) 77, (LEFT) 75" are displayed, and for the ankle, "MAXIMUM: (RIGHT) 131, (LEFT) 136", "MINIMUM: (RIGHT) 78, (LEFT) 73" are displayed.

Figure 9:
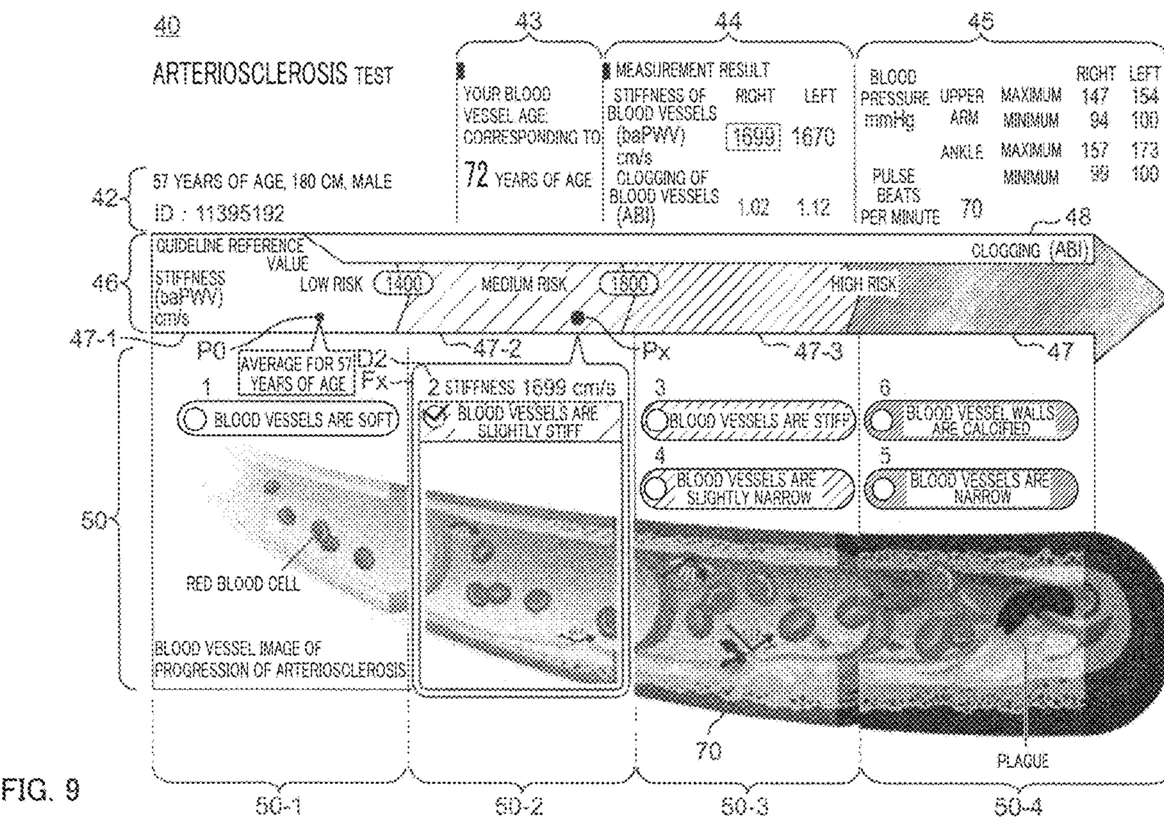
FIG. 9 shows Display Example 2 by the blood pressure pulse wave measurement apparatus.
Figure 10:
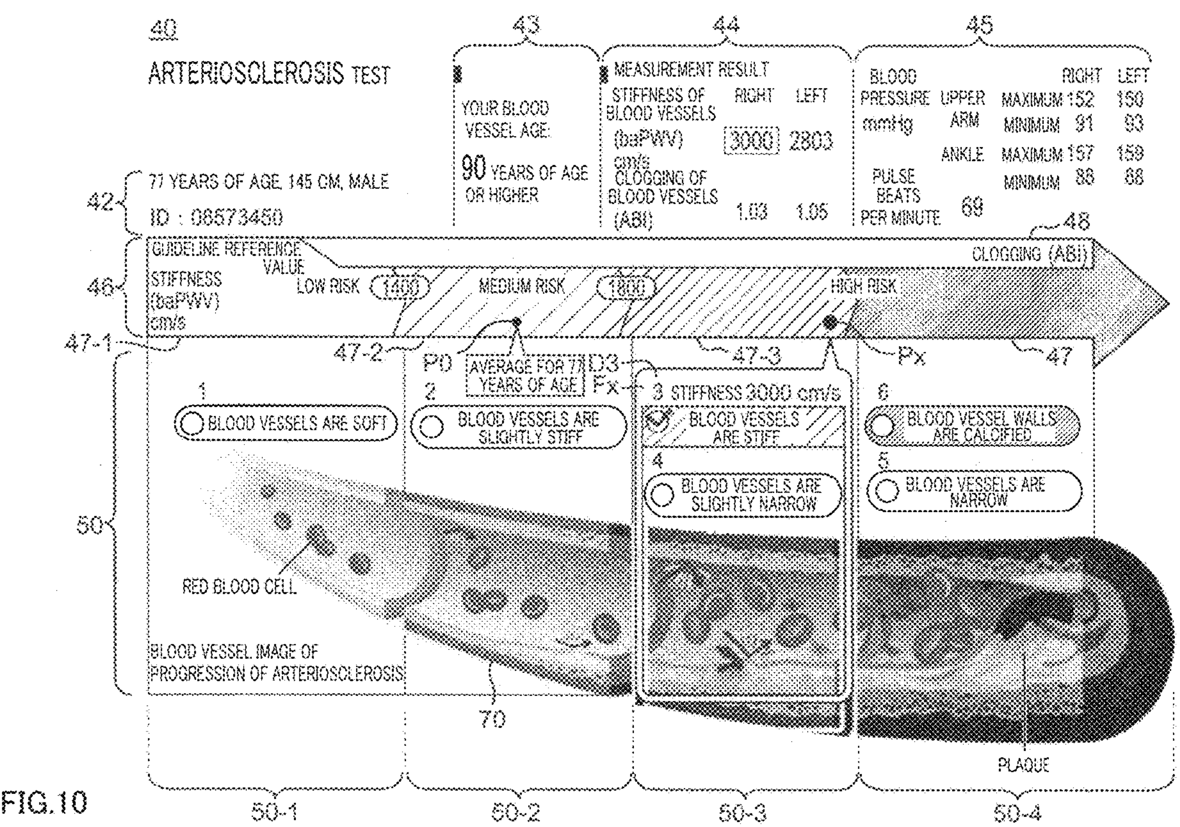
FIG. 10 shows Display Example 3 by the blood pressure pulse wave measurement apparatus.

One-dimensional graph 46 includes right-pointing wide arrow 47 for indicating brachial-ankle pulse wave velocity baPWV that is an index representing "stiffness of blood vessels", and right-pointing wide arrow 48 for indicating ankle brachial index ABI that is an index representing "clogging of blood vessels". Arrows 47, 48 overlap in a width direction (direction perpendicular to the direction of the arrows). In arrow 47, "STIFFNESS OF BLOOD VESSELS" (baPWV) CM/S" is displayed, and in arrow 48, "CLOGGING OF BLOOD VESSELS (ABI)" is displayed. Hereinafter, arrow 47 is referred to as "baPWV index", and arrow 48 is referred to as "ABI index". In FIGS. 8 to 10, baPWV index 47 is displayed on the front side, and ABI index 48 is displayed on the back side and almost hidden. On the other hand, in FIGS. 11 to 13, ABI index 48 is displayed on the front side, and baPWV index 47 is displayed on the back side and almost hidden. This will be described later in detail.

Figure 11:
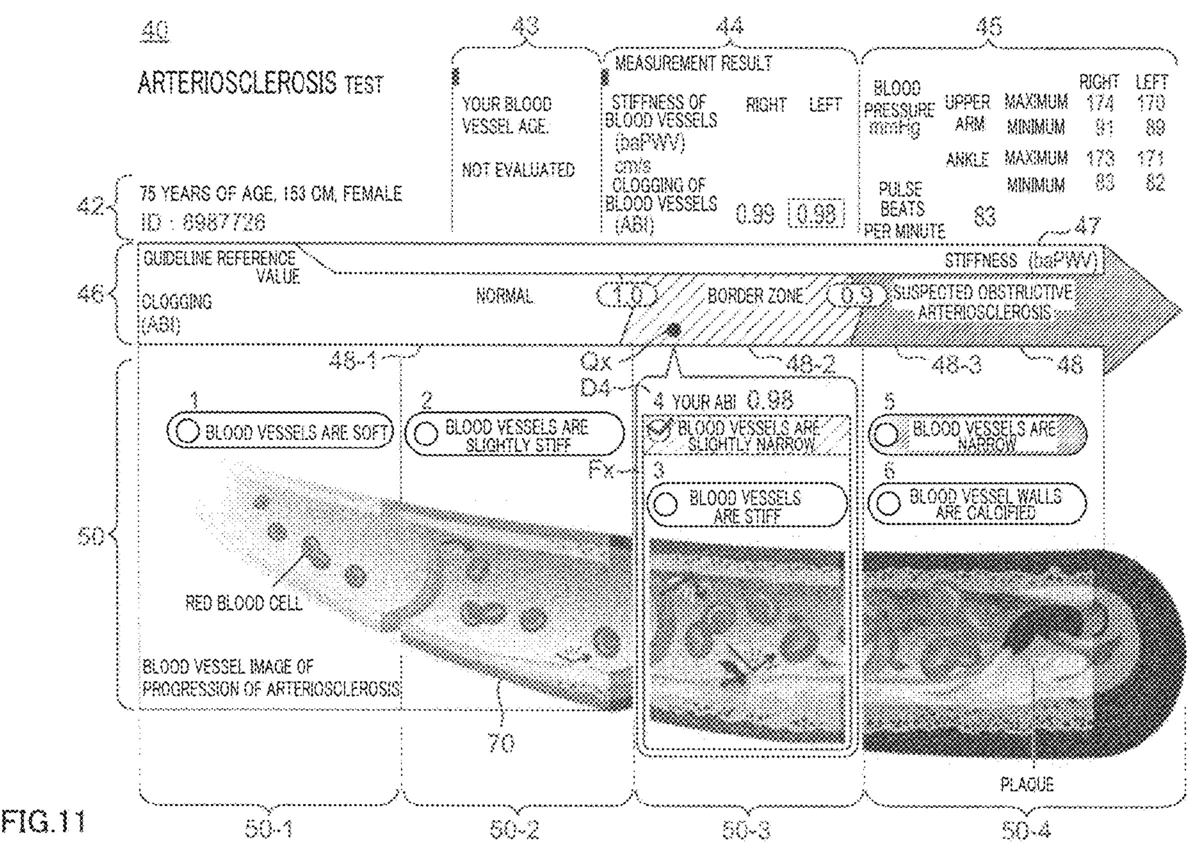
FIG. 11 shows Display Example 4 by the blood pressure pulse wave measurement apparatus.

For example, as shown in FIG. 8, baPWV index 47 is divided into three regions (denoted by reference numerals 47-1, 47-2, 47-3) of "low risk", "medium risk", and "high risk" with respect to the direction of the arrow. Also, for example, as shown in FIG. 11, ABI index 48 is divided into three regions (denoted by reference numerals 48-1, 48-2, 48-3) of "normal", "border zone", and "suspected obstructive arteriosclerosis".

Figure 7:
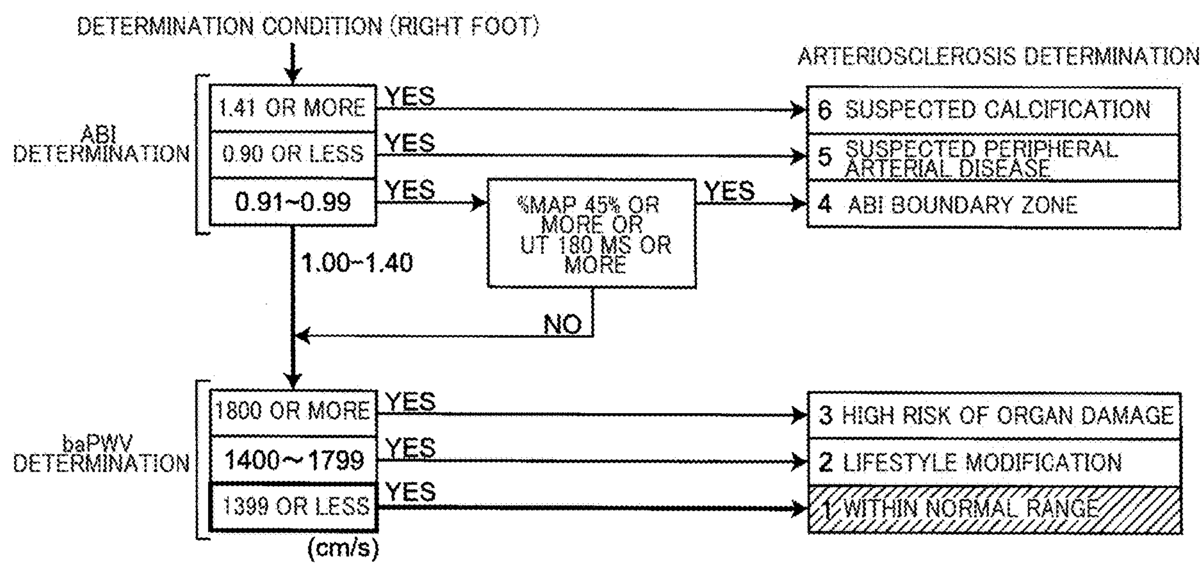
FIG. 7 is the Steno-Stiffness chart for determining a progress stage of arteriosclerosis.

Regions 47-1 to 47-3 and 48-1 to 48-3 correspond to "DETERMINATION CONDITION (RIGHT FOOT)" in the Steno-Stiffness chart in FIG. 7 for determining the progress stage of arteriosclerosis (the same applies to a determination condition for the left foot). Specifically, "low risk" region 47-1, "medium risk" region 47-2, and "high risk" region 47-3 in baPWV index 47 in FIGS. 8 to 10 correspond to ranges of brachial-ankle pulse wave velocity baPWV of "1399 or less", "1400 to 1799", and "1800 or more", respectively as shown in a lower left part ("baPWV DETERMINATION" part) in FIG. 7. Accordingly, for example, in FIG. 8, "1400" is displayed on a borderline between "low risk" region 47-1 and "medium risk" region 47-2. Also, "1800" is displayed on a borderline between "medium risk" region 47-2 and "high risk" region 47-3. "Normal" region 48-1, "border zone" region 48-2, and "suspected obstructive arteriosclerosis" region 48-3 in ABI index 48 in FIGS. 11 to 13 correspond to ranges of ankle brachial index ABI of "1.00 to 1.40", "0.91 to 0.99", and "0.90 or less", respectively, as shown in an upper left part ("ABI DETERMINATION" part) in FIG. 7. Accordingly, for example, in FIG. 11, "1.0" is displayed on a borderline between "normal" region 48-1 and "border zone" region 48-2. Also, "0.9" is displayed on a borderline between "border zone" region 48-2 and "suspected obstructive arteriosclerosis" region 48-3. As shown in FIG. 7, ankle brachial index ABI of "1.41 or more" corresponds to a progress stage of arteriosclerosis of "6 SUSPECTED CALCIFICATION" as a particularly severe condition. ABI=0.90, 1.00, and 1.40 are referred to as a first threshold, a second threshold, and a third threshold, respectively, with two decimal places as significant digits.

Image block 50 in FIG. 8 is divided into four image regions (denoted by reference numerals 50-1, 50-2, 50-3, and 50-4) along one-dimensional graph 46. "1 (circle) BLOOD VESSELS ARE SOFT" D1 is displayed in image region 50-1 at a left end, "2 (circle) BLOOD VESSELS ARE SLIGHTLY STIFF" D2 is displayed in image region 50-2 on the right of image region 50-1, "3 (circle) BLOOD VES- SELS ARE STIFF" D3 and "4 (circle) BLOOD VESSELS ARE SLIGHTLY NARROW" D4 are displayed in image region 50-3 on the right of image region 50-2, and "5 (circle) BLOOD VESSELS ARE NARROW" D5 and "6 (circle) BLOOD VESSEL WALLS ARE CALCIFIED" D6 are displayed in image region 50-4 on the most right side.

Displays D1 to D6 correspond to determination results ("ARTERIOSCLEROSIS DETERMINATION" part in the right half in FIG. 7) in the Steno-Stiffness chart in FIG. 7. Specifically, display D1 "1 (circle) BLOOD VESSELS ARE SOFT", display D2 "2 (circle) BLOOD VESSELS ARE SLIGHTLY STIFF", display D3 "3 (circle) BLOOD VESSELS ARE STIFF", display D4 "4 (circle) BLOOD VESSELS ARE SLIGHTLY NARROW", display D5 "5 (circle) BLOOD VESSELS ARE NARROW" and display D6 "6 (circle) BLOOD VESSEL WALLS ARE CALCIFIED" in FIG. 8 correspond to the determination results: "1 WITHIN NORMAL RANGE", "2 LIFESTYLE MODIFICATION", "3 HIGH RISK OF ORGAN DAMAGE", "4 ABI BOUNDARY ZONE", "5 SUSPECTED PERIPHERAL ARTERIAL DISEASE", and "6 SUSPECTED CALCIFICATION", respectively, in FIG. 7.

In image block 50 in FIG. 8, across four image regions 50-1, 50-2, 50-3, 50-4 along one-dimensional graph 46, illustration 70 representing a state of blood vessels corresponding to display D1 to D6 in the image regions, and a title of illustration 70 "BLOOD VESSEL IMAGE OF PROGRESSION OF ARTERIOSCLEROSIS" 51 are displayed. Illustration 70 includes blood vessel 61, and red blood cells (representing blood) 62 flowing through blood vessel 61. LDL cholesterol or neutral fat 63 deposited on an inner wall of blood vessel 61 is thicker from image region 50-1 toward image region 50-4. Thus, the illustration shows that as arteriosclerosis progresses, red blood cells 62 collide 69 with the inner wall of blood vessel 61 to gradually prevent flow. Further, in image region 50-4, plaque 64 is shown on the inner wall of blood vessel 61. As such, since illustration 70 according to the progress stage of arteriosclerosis is displayed in addition to one-dimensional graph 46, the progress stage of arteriosclerosis can be displayed to be more intuitively understandable by the ordinary patient etc.

On display screen 40, for example, an illustration showing measurement sites (right ankle, left ankle, right upper arm, left upper arm) in the human body may be additionally displayed. Also, development of brachial-ankle pulse wave velocity baPWV measured in the past (trend graph) may be additionally displayed.

Next, display examples displayed on display screen 40 will be described in detail.

Display Example 1

FIG. 8 shows a display example when stiffness of blood vessels (baPWV) is 1398 cm/s, clogging of blood vessels (ABI) is 1.16 for the right side of the body of a subject (ID: 5611458) as emphasized in measurement result block 44 (display enclosed by a rectangular frame, hereinafter the same). In this case, ABI corresponds to "1.00 to 1.40" as "normal" in the "ABI DETERMINATION" part in FIG. 7. Further, baPWV corresponds to 1399 cm/s or less in the "baPWV DETERMINATION" part in FIG. 7. Accordingly, the progress stage of arteriosclerosis is determined as "1 WITHIN NORMAL RANGE".

According to the determination result, particularly to ABI exceeding the first threshold of 0.90, baPWV index 47 is displayed on the front side, and ABI index 48 is displayed on the back side and almost hidden in one-dimensional graph 46 in FIG. 8. Further, on "low risk" region 47-1 in baPWV index 47, point Px representing baPWV=1398 cm/s is displayed.

Image region 50-1 in FIG. 8 is enclosed by determination result display frame Fx. In determination result display frame Fx, display D1 "1 (circle) BLOOD VESSELS ARE SOFT" and a part corresponding to the determination result in illustration 70 are included. A check mark is placed in the circle in display D1. For emphasis, "STIFFNESS 1398 CM/S" is displayed at the top of determination result display frame Fx.

Display Example 2

FIG. 9 shows a display example when stiffness of blood vessels (baPWV) is 1699 cm/s, clogging of blood vessels (ABI) is 1.02 for the right side of the body of a subject (ID: 11395192) as emphasized in measurement result block 44. Also in this case, ABI corresponds to "1.00 to 1.40" as "normal" in the "ABI DETERMINATION" part in FIG. 7. Further, baPWV corresponds to 1400 to 1799 cm/s in the "baPWV DETERMINATION" part in FIG. 7. Accordingly, the progress stage of arteriosclerosis is determined as "2 LIFESTYLE MODIFICATION".

According to the determination result, particularly to ABI exceeding the first threshold of 0.90, baPWV index 47 is displayed on the front side, and ABI index 48 is displayed on the back side and almost hidden in one-dimensional graph 46 in FIG. 9. Further, on "medium risk" region 47-2 in baPWV index 47, point Px representing baPWV=1699 cm/s is displayed. Also, on "low risk" region 47-1 in baPWV index 47, point PO representing average baPWV of a human of the same age as subject 200 (in this case, 57 years of age) is displayed. The display of point PO is omitted in FIG. 8 (when the progress stage of arteriosclerosis is "1 WITHIN NORMAL RANGE").

Image region 50-2 in FIG. 9 is enclosed by determination result display frame Fx. In determination result display frame Fx, display D2 "2 (circle) BLOOD VESSELS ARE SLIGHTLY STIFF" and a part corresponding to the determination result in illustration 70 are included. A check mark is placed in the circle in display D2. For emphasis, "STIFFNESS 1699 CM/S" is displayed at the top of determination result display frame Fx.

Display Example 3

FIG. 10 shows a display example when stiffness of blood vessels (baPWV) is 5000 cm/s, clogging of blood vessels (ABI) is 1.03 for the right side of the body of a subject (ID: 08573450) as emphasized in measurement result block 44. Also in this case, ABI corresponds to "1.00 to 1.40" as "normal" in the "ABI DETERMINATION" part in FIG. 7. Further, baPWV corresponds to 1800 cm/s or more in the "baPWV DETERMINATION" part in FIG. 7. Accordingly, the progress stage of arteriosclerosis is determined as "3 HIGH RISK OF ORGAN DAMAGE".

According to the determination result, particularly to ABI exceeding the first threshold of 0.90, baPWV index 47 is displayed on the front side, and ABI index 48 is displayed on the back side and almost hidden in one-dimensional graph 46 in FIG. 10. Further, on "high risk" region 47-3 in baPWV index 47, point Px representing baPWV=3000 cm/s is displayed. Also, on "medium risk" region 47-2 in baPWV index 47, point PO representing average baPWV of a human of the same age as subject 200 (in this case, 77 years of age) is displayed.

Image region 50-3 in FIG. 10 is enclosed by determination result display frame Fx. In determination result display frame Fx, display D3 "3 (circle) BLOOD VESSELS ARE STIFF" (and display D4 "4 (circle) BLOOD VESSELS ARE SLIGHTLY NARROW") and a part corresponding to the determination result in illustration 70 are included. A check mark is placed in the circle in display D3. For emphasis, "STIFFNESS 3000 CM/S" is displayed at the top of determination result display frame Fx.

Display Example 4

FIG. 11 shows a display example when clogging of blood vessels (ABI) is 0.98 for the left side of the body of a subject (ID: 8987726) as emphasized in measurement result block 44. In this case, ABI corresponds to 0.91 to 0.99 (specifically, more than the first threshold of 0.90 and less than the second threshold of 1.00) in the "ABI DETERMINATION" part in FIG. 7. At this time, the determination results differ depending on whether normalized pulse wave area % MAP is 45% or more or whether upstroke time UT is 180 ms or more. In this example, % MAP of subject 200 is 45% or more, or upstroke time UT is 180 ms or more (not shown), and thus the progress stage of arteriosclerosis in FIG. 7 is determined as "4 ABI border zone".

According to the determination result, ABI index 48 is displayed on the front side, and baPWV index 47 is displayed on the back side and almost hidden in one-dimensional graph 46 in FIG. 11. Further, on "border zone" region 48-2 in ABI index 48, point Qx representing ABI=0.98 is displayed.

Image region 50-3 in FIG. 11 is enclosed by determination result display frame Fx. In determination result display frame Fx, display D4 "4 (circle) BLOOD VESSELS ARE SLIGHTLY NARROW" (and display D3 "3 (circle) BLOOD VESSELS ARE STIFF") and a part corresponding to the determination result in illustration 70 are included. A check mark is placed in the circle in display D4. For emphasis, "YOUR ABI 0.98" is displayed at the top of determination result display frame Fx.

For the subject (ID: 8987726) in FIG. 11, if % MAP is less than 45% and upstroke time UT is less than 180 ms, the progress stage of arteriosclerosis is determined as any of "1 WITHIN NORMAL RANGE" to "3 HIGH RISK OF ORGAN DAMAGE" according to the value of baPWV in the "baPWV DETERMINATION" part in FIG. 7. In that case, similarly to the examples in FIGS. 8 to 10, baPWV index 47 is displayed on the front side, and ABI index 48 is displayed on the back side and almost hidden in one-dimensional graph 46. Further, similarly to the examples in FIGS. 8 to 10, point Px representing baPWV is displayed on baPWV index 47. This allows baPWV index 47 and ABI index 48 to be properly switched on one-dimensional graph 46 according to the Steno-Stiffness chart.

Display Example 5

Figure 12:
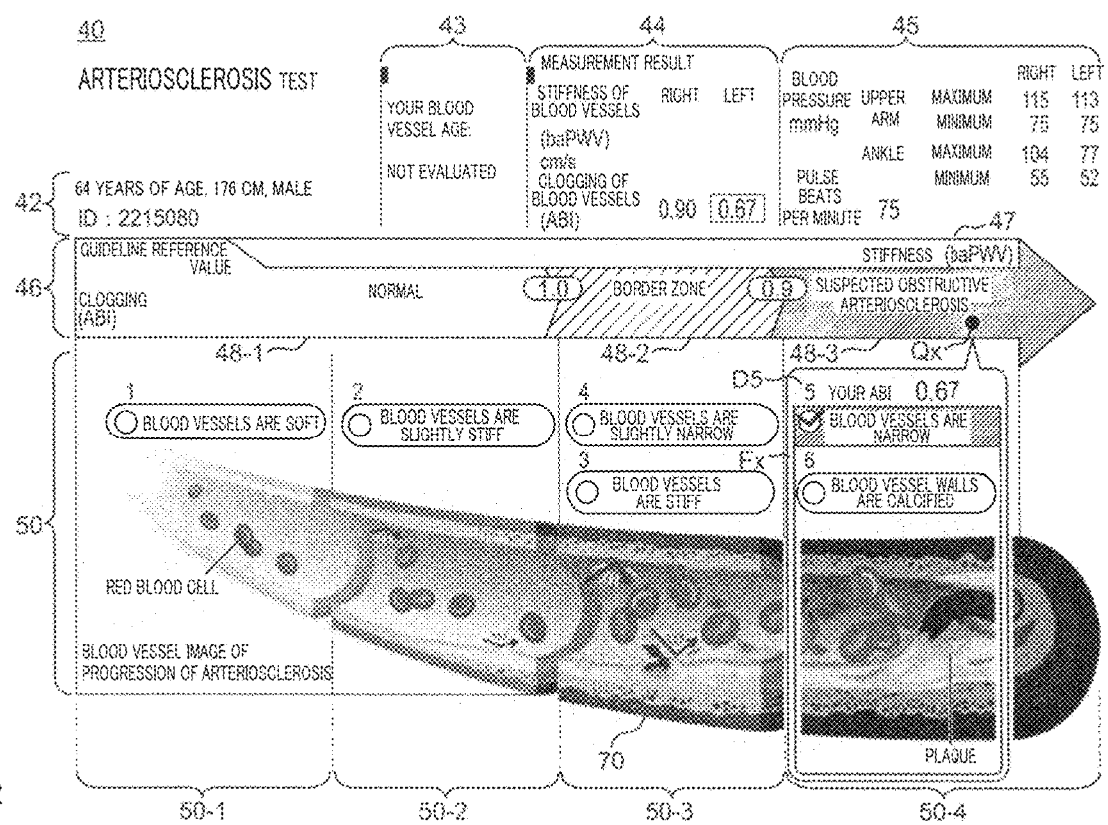
FIG. 12 shows Display Example 5 by the blood pressure pulse wave measurement apparatus.

FIG. 12 shows a display example when clogging of blood vessels (ABI) is 0.67 for the left side of the body of a subject (ID: 2215080) as emphasized in measurement result block 44. In this case, ABI corresponds to the first threshold of 0.90 or less in the "ABI DETERMINATION" part in FIG. 7. Accordingly, the progress stage of arteriosclerosis is determined as "5 SUSPECTED PERIPHERAL ARTERIAL DISEASE".

According to the determination result, particularly to ABI being the first threshold of 0.90 or less, ABI index 48 is displayed on the front side, and baPWV index 47 is displayed on the back side and almost hidden in one-dimensional graph 46 in FIG. 12. Further, on "suspected obstructive arteriosclerosis" region 48-3 in ABI index 48, point Qx representing ABI=0.67 is displayed.

Image region 50-4 in FIG. 11 is enclosed by determination result display frame Fx. In determination result display frame Fx, display D5 "5 (circle) BLOOD VESSELS ARE NARROW" (and display D6 "6 (circle) BLOOD VESSEL WALLS ARE CALCIFIED") and a part corresponding to the determination result in illustration 70 are included. A check mark is placed in the circle in display D5. For emphasis, "YOUR ABI 0.67" is displayed at the top of determination result display frame Fx.

Display Example 6

Figure 13:
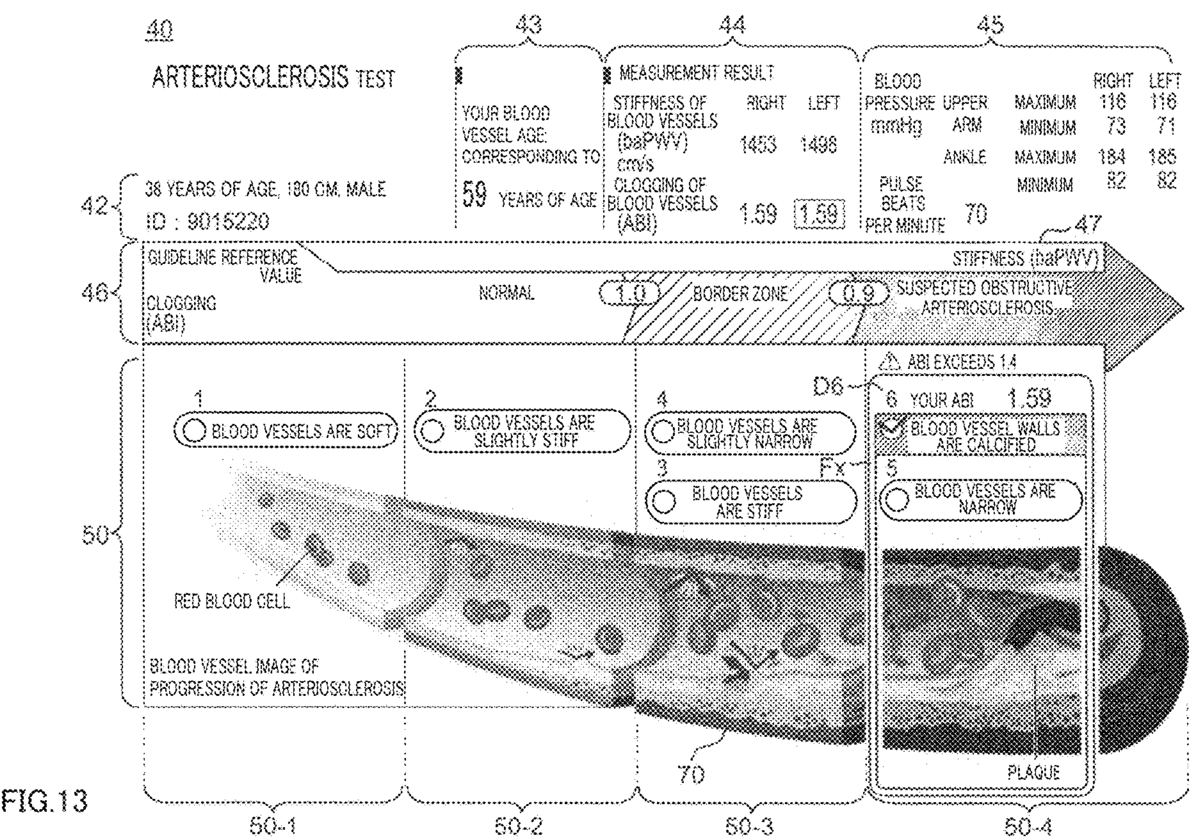
FIG. 13 shows Display Example 6 by the blood pressure pulse wave measurement apparatus.

FIG. 13 shows a display example when clogging of blood vessels (ABI) is 1.59 for the left side of the body of a subject (ID: 9015220) as emphasized in measurement result block 44. In this case, ABI corresponds to 1.41 or more (that is, more than the first threshold of 1.40) in the "ABI DETERMINATION" part in FIG. 7. Accordingly, the progress stage of arteriosclerosis is determined as "6 SUSPECTED CALCIFICATION".

According to the determination result, particularly to ABI being more than the first threshold of 1.40, ABI index 48 is displayed on the front side, and baPWV index 47 is displayed on the back side and almost hidden in one-dimensional graph 46 in FIG. 13. Further, on "suspected obstructive arteriosclerosis" region 48-3 in ABI index 48, point Qx representing ABI=1.59 is displayed.

Image region 50-4 in FIG. 11 is enclosed by determination result display frame Fx. In determination result display frame Fx, display D6 "6 (circle) BLOOD VESSEL WALLS ARE CALCIFIED" (and display D5 "5 (circle) BLOOD VESSELS ARE NARROW") and a part corresponding to the determination result in illustration 70 are included. A check mark is placed in the circle in display D5. For emphasis, "YOUR ABI 1.59" is displayed at the top of determination result display frame Fx. Further, for warning, "ABI EXCEEDS 1.4" is displayed between determination result display frame Fx and one-dimensional graph 46. Thus, it can be notified that subject 200 is in a particularly severe condition with calcified blood vessels.

As such, in blood pressure pulse wave measurement apparatus 100, when ankle brachial index ABI of subject 200 exceeds the first threshold of 0.90, that is, at a relatively early stage of the progress of arteriosclerosis, the point representing brachial-ankle pulse wave velocity baPWV is displayed on one-dimensional graph 46. On the other hand, when ankle brachial index ABI of subject 200 is the first threshold of 0.90 or less, that is, at a later stage of the progress of arteriosclerosis, the point representing ankle brachial index ABI instead of the point representing brachial-ankle pulse wave velocity baPWV is displayed on one-dimensional graph 46. Specifically, in accordance with the progress stage of arteriosclerosis, point Px representing brachial-ankle pulse wave velocity baPWV to be noted and point Qx representing ankle brachial index ABI to be noted are switched and displayed on one-dimensional graph 46. As a result, the ordinary patient etc. can easily understand the progress stage of arteriosclerosis according to the coordinate position of point Px or Qx displayed on one-dimensional graph 46. As such, with blood pressure pulse wave measurement apparatus 100, the progress stage of arteriosclerosis can be displayed to be intuitively understandable by the ordinary patient etc.

Also, in blood pressure pulse wave measurement apparatus 100, the first threshold of ankle brachial index ABI is set to 0.90. Thus, brachial-ankle pulse wave velocity baPWV and ankle brachial index ABI can be properly switched on one-dimensional graph 46 according to the Steno-Stiffness chart (FIG. 7).

In blood pressure pulse wave measurement apparatus 100, a scale of one-dimensional graph 46 is set so that point Px representing baPWV on baPWV index 47 and point Qx representing ABI on ABI index 48 gradually move in the same direction. Thus, the progress stage of arteriosclerosis can be displayed to be more intuitively understandable by the ordinary patient etc.

Point Px representing baPWV on baPWV index 47 and point Qx representing ABI on ABI index 48 may substantially represent only the points on baPWV index 47 and ABI index 48, that is, the coordinate positions. For example, to represent the "points", various symbols such as a circle or a triangle, marks, or the like may be used.

In this embodiment, the configuration in which pressure sensor 28 is used to detect a pulse wave has been described, however, an arterial volume sensor (not shown) may be used to detect a pulse wave. In this case, the arterial volume sensor may include, for example, a light emitting element that emits light to the artery, and a light receiving element that receives the light emitted by the light emitting element and transmitted through or reflected by the artery. Alternatively, the arterial volume sensor may include a plurality of electrodes, pass a certain minute electric current through a measurement site of subject 200, and detect changes in voltage caused by changes in impedance resulting from propagation of a pulse wave (bioimpedance).

In this embodiment, brachial-ankle pulse wave velocity baPWV and ankle brachial index ABI are measured and obtained, but not limited to this. Measured brachial-ankle pulse wave velocity baPWV and ankle brachial index ABI may be input and obtained through, for example, a network such as the Internet or local area network.

The display method performed by blood pressure pulse wave measurement apparatus 100 described above may be recorded as application software (computer programs) on a recording medium capable of non-transitorily storing data such as a compact disc (CD), digital versatile disk (DVD), or flash memory. The application software recorded on the recording medium may be installed in a substantial computer apparatus such as a personal computer, personal digital assistant (PDA), or smartphone to cause the computer apparatus to perform the method described above.

The embodiments described above are illustrative and various modifications may be made without departing from the scope of the present invention. The embodiments described above may stand solely, but may be combined with each other. Various features in different embodiments may also stand solely, but the features in the different embodiments may be combined with each other.

REFERENCE SIGNS LIST

40 display screen
46 one-dimensional graph
47 baPWV index
48 ABI index
70 illustration
Fx determination result display frame
Px, Qx point

The invention claimed is:

1. A blood pressure pulse wave measurement apparatus for displaying a progress stage of arteriosclerosis of a subject, the apparatus comprising:

a pair of first cuffs for pressing part of upper limbs of a subject;

a pair of second cuffs for pressing part of lower limbs of the subject;

a pair of first tubes and a pair of second tubes connected to the pair of first cuffs and the pair of second cuffs, respectively;

a processor that is connected to the pair of first cuffs via the pair of first tubes and is connected to the pair of second cuffs via the pair of second tubes; and a display screen or a printer which is connected to the processor wherein the processor is configured to:

obtain a pulse wave velocity that is an index representing stiffness of blood vessels of the subject and is calculated by using a first pulse wave propagating through the pair of first tubes and a second pulse wave propagating through the pair of second tubes, obtain a lower/upper limb blood pressure ratio that is an index representing clogging of blood vessels of the subject and is calculated by using the first pulse wave and the second pulse wave, perform processing to display a point representing the pulse wave velocity on a one-dimensional graph on the display screen or to output the point on the one-dimensional graph to the printer when the lower/upper limb blood pressure ratio of the subject exceeds a first threshold, the first threshold being predefined, and to display a point representing the lower/upper limb blood pressure ratio instead of the point representing the pulse wave velocity on the one-dimensional graph on the display screen or to output the point on the one-dimensional graph to the printer when the lower/upper limb blood pressure ratio of the subject is the first threshold or less, perform processing to display contents of an arteriosclerosis determination with the one-dimensional graph on the display screen or to output the contents of the arteriosclerosis determination of the subject with the one-dimensional graph to the printer, and perform processing to switch the contents of the arteriosclerosis determination to be displayed on the display screen or be output to the printer according to a measurement value of the lower/upper limb blood pressure ratio of the subject.

2. The blood pressure pulse wave measurement apparatus according to claim 1, wherein the first threshold of an ankle brachial index (ABI) as the lower/upper limb blood pressure ratio is set to 0.90 based on a Steno-Stiffness chart for determining the progress stage of arteriosclerosis.

3. The blood pressure pulse wave measurement apparatus according to claim 2, wherein the processor is further configured to:

obtain an upstroke time (UT) of a pulse wave in the ankle of the subject, and obtain a normalized pulse wave area (% MAP) of a waveform of the pulse wave in the ankle of the subject, wherein the processor is further configured to perform processing to display a point representing the ankle brachial index (ABI) as the lower/upper limb blood pressure ratio instead of the point representing the pulse wave velocity on the one-dimensional graph on the display screen or to output the point on the one-dimensional graph to the printer, when the upstroke time (UT) is 180 milliseconds or more in the case where the ankle brachial index (ABI) is more than the first threshold of 0.90 and less than a second threshold of 1.00, or when the normalized pulse wave area (% MAP) is 45% or more in the case where the ankle brachial index (ABI) is more than the first threshold of 0.90 and less than the second threshold of 1.00.

4. The blood pressure pulse wave measurement apparatus according to claim 2, wherein the processor is further configured to perform processing to display an element to represent blood vessels being calcified on the display screen or to output the element to the printer if the ankle brachial index (ABI) exceeds a third threshold of 1.40.

5. The blood pressure pulse wave measurement apparatus according to claim 1, wherein the processor is further configured to perform processing to display an illustration representing a state of blood vessels on the display screen or to output the illustration to the printer according to the progress stage of arteriosclerosis in addition to the one-dimensional graph.

6. A non-transitory computer-readable recording medium storing therein a program for causing a computer to perform a method of displaying a progress stage of arteriosclerosis of a subject and is included in a blood pressure pulse wave measurement apparatus comprising:

a pair of first cuffs for pressing part of upper limbs of a subject;

a pair of second cuffs for pressing part of lower limbs of the subject;

a pair of first tubes and a pair of second tubes connected to the pair of first cuffs and the pair of second cuffs, respectively;

a processor that is connected to the pair of first cuffs via the pair of first tubes and is connected to the pair of second cuffs via the pair of second tubes; and a display screen or a printer which is connected to the processor, the method comprises the program causing the computer to perform:

obtainment processing that obtains a pulse wave velocity that is an index representing stiffness of blood vessels of the subject, and obtains a lower/upper limb blood pressure ratio that is an index representing clogging of blood vessels of the subject;

display processing that displays a point representing the pulse wave velocity on a one-dimensional graph on the display screen or output processing that outputs the point on the one-dimensional graph to the printer when the lower/upper limb blood pressure ratio of the subject exceeds a first threshold, the first threshold being predefined, and to display a point representing the lower/upper limb blood pressure ratio instead of the point representing the pulse wave velocity on the one-dimensional graph on the display screen or to output the point on the one-dimensional graph to the printer when the lower/upper limb blood pressure ratio of the subject is the first threshold or less;

perform processing that displays contents of an arteriosclerosis determination with the one-dimensional graph on the display screen or output processing that outputs the contents of the arteriosclerosis determination of the subject with the one-dimensional graph to the printer, and switch processing that switches the contents of the arteriosclerosis determination to be displayed on the display screen or be output to the printer according to a measurement value of the lower/upper limb blood pressure ratio of the subject.

* * * * *